United States Patent [19]

Nakazato et al.

[11] Patent Number: 5,502,202

[45] Date of Patent: Mar. 26, 1996

[54] AMINOALKYLTHIAZOLE DERIVATIVE

[75] Inventors: Atsuro Nakazato; Yoshinori Sekiguchi, both of Saitama; Yutaka Kawashima, Gunma; Katsuo Hatayama, Saitama, all of Japan

[73] Assignee: Taisho Pharmaceutical Co., Ltd., Japan

[21] Appl. No.: 142,471

[22] PCT Filed: May 29, 1992

[86] PCT No.: PCT/JP92/00702

§ 371 Date: Nov. 29, 1993

§ 102(e) Date: Nov. 29, 1993

[87] PCT Pub. No.: WO92/21667

PCT Pub. Date: Dec. 10, 1992

[30] Foreign Application Priority Data

May 30, 1991 [JP] Japan ................................. 3-228144

[51] Int. Cl.$^6$ .................................................. C07D 277/40
[52] U.S. Cl. ............................................................. 548/198
[58] Field of Search ............................................... 548/198

[56] References Cited

U.S. PATENT DOCUMENTS 3,210,368 10/1965 Huebner ............................. 260/306 S

OTHER PUBLICATIONS

Chemical Abstracts, vol. 85, No. 3, 19 Jul. 1976 Abstract No. 21184h.

*Primary Examiner*—Robert Gerstl

[57] ABSTRACT

Object: To provide an antipsychotic drug being different in functional mechanism from dopamine autoreceptor agonists, namely, to provide an antipsychotic drug having a specific affinity for a sigma receptor and causing no extrapyramidal disorder.

Constitution: An aminoalkylthiazole derivative represented by formula:

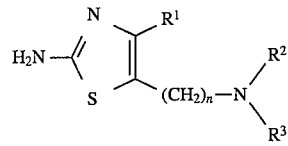

(wherein $R^1$ represents a phenyl group substituted with a halogen atom; $R^2$ and $R^3$ are either the same or different and each represents an alkyl group having 4 to 10 carbon atoms; and n is 2 or 3;) and a salt thereof.

2 Claims, No Drawings

AMINOALKYLTHIAZOLE DERIVATIVE

This application is a 371 of PCT/JP92/00702 filed May 29, 1992.

TECHNICAL FIELD

This invention relates to an aminoalkylthiazole derivative which acts on a sigma receptor and exhibits an antipsychotic action.

BACKGROUND ART

Antipsychotic drugs have been used not only in the treatment of schizophrenia but also in the treatment of troublesome behaviors (for example, aggressive actions, mental excitation, dromomania, delirium) caused by cerebrovascular disorders or senile dementia. However, conventional antipsychotic drugs are accompanied by severe extrapyramidal disorders as side effects, which results in a serious problem.

In recent years, there have been made approaches for developing antipsychotic drugs from a viewpoint completely differing from the functional mechanism of the conventional drugs to thereby solve the above-mentioned problem. One of these approaches includes the use of a sigma receptor antagonist. A compound having a specific affinity for a sigma receptor, which is considered as an receptor participating in mental symptoms such as hallucinosis, exhibits an antipsychotic action without causing any extrapyramidal disorders.

There has been known talipexole (a compound described in JP-B-52-46236) as an antipsychotic drug having a thiazole skeleton. It is reported that this compound is a selective dopamine autoreceptor agonist and suppresses nerve ignition and biosynthesis and liberation of dopamine by stimulating the presynaptic autoreceptor, thus depressing the function of the dopamine nerve system, which closely relates to the outbreak of schizophrenia [European Journal of Pharmacology, 166, 303–305 (1989); Acta Pharmaceut. Suec. Suppl., 1, 154–164 (1983)].

However, it cannot be expected too much of talipexole of being highly effective on positive symptoms of schizophrenia, similar to other conventionally known selective dopamine autoreceptor agonists. In addition, the effect of talipexole on negative symptoms of this disease had not been definitely confirmed [Toshiya Inada et al., Shinkei Seishin Yakuri, 13, 75–77 (1990)].

In contrast thereto, the compound of the present invention has an affinity for a sigma receptor. Thus it is considered as being different from the dopamine autoreceptor agonists in functional mechanism.

An object of the present invention is to provide an antipsychotic drug which is different from dopamine autoreceptor agonists in functional mechanism, namely, an antipsychotic drug having a specific affinity for a sigma receptor and causing no extrapyramidal disorder.

DISCLOSURE OF THE INVENTION

The present inventors have conducted extensive studies on compounds having a thiazole skeleton. As a result, they have found a novel 2-amino-4-aryl-5-substituted aminoalkylthiazole derivative showing a specific and high affinity for a sigma receptor, thus completing the present invention.

Accordingly, the present invention provides an aminoalkylthiazole derivative represented by the following formula:

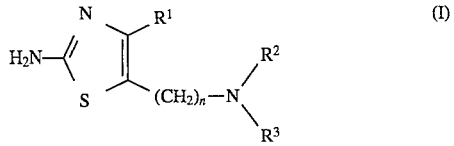

(wherein $R^1$ represents a phenyl group substituted with a halogen atom; $R^2$ and $R^3$ are either the same or different and each represents an alkyl group having 4 to 10 carbon atoms; and n is 2 or 3;) and a salt thereof.

In the present invention, the term "alkyl group" means a straight chain or branched alkyl group, while the term "halogen atom" means a fluorine, chlorine, bromine or iodine atom.

The term "salt of the compound of the formula (I)" means a pharmaceutically acceptable salt, for example, salts with inorganic acids such as sulfuric acid, hydrochloric acid, bromic acid and phosphoric acid, and salts with organic acids such as acetic acid, lactic acid, tartaric acid, fumaric acid, maleic acid, trifluoroacetic acid, methanesulfonic acid and tosylic acid.

Preferred compounds according to the present invention are those represented by formula (I) wherein $R^1$ is a phenyl group substituted with a halogen atom at the 4-position and $R^2$ and $R^3$ are the same and each represents an alkyl group having 5 to 8 carbon atoms. Examples thereof include 2-amino-4-(4-bromophenyl)-5-(2-di-n-pentylamino-ethyl)thiazole dihydrochloride, 2-amino-4-(4-bromophenyl)-5-( 2-di-n-hexylaminoethyl)thiazole dihydrochloride, 2-amino-4-( 4-chlorophenyl)-5-(2-di-n-hexylaminoethyl)thiazole, 2-amino- 5-(2-di-n-hexylaminoethyl)-4-(4-fluorophenyl)thiazole dihydrochloride and 2-amino-4-(4-bromophenyl)-5-(2-di-n-octylaminoethyl)thiazole dihydrochloride.

The compound of formula (I) can be prepared by, for example, the following method (in the reaction scheme, X represents an optional halogen atom and $R^1$, $R^2$ and $R^3$ are as defined above).

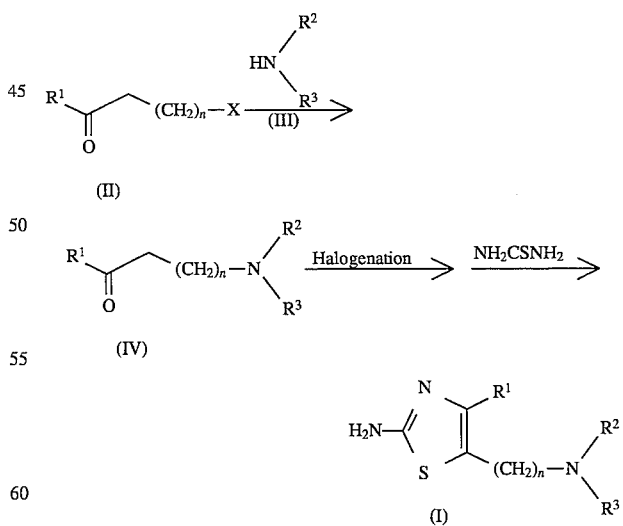

First, a compound of formula (II) is reacted with an amine of formula (III) without using any solvents or in an inert solvent to thereby give a compound of formula (IV). In this reaction, a base may be used. Examples of the base to be used in this reaction include inorganic bases such as potassium carbonate, sodium carbonate and sodium hydrogencarbonate and organic bases such as triethylamine, diisopropylethylamine and pyridine. Examples of the solvent include alcohols such as ethanol, ethers such as dioxane and 1,2-dimethoxyethane, benzene, toluene, xylene, acetonitrile, N,N-dimethylformamide and dimethylsulfoxide. The reaction is carried out at a temperature of from room temperature to 170° C. for 1 to 24 hours under stirring, preferably at 60° to 140° C. for 2 to 12 hours under stirring.

Next, the compound of formula (IV) is converted into its bromate or hydrochloride and then reacted with a halogen such as bromine in a solvent. After distilling off the solvent, it is further reacted with thiourea in a solvent. Thus the compound of the present invention can be obtained. Examples of the solvent to be used in the reaction with a halogen include organic carboxylic acids such as acetic acid, alcohols such as ethanol, chloroform, dichloromethane, dimethylformamide and water. This reaction is carried out at a temperature of from −40° C. to room temperature for 0.5 to 5 hours under stirring, preferably at a temperature of from 0° C. to room temperature for 0.5 to 2 hours under stirring. Examples of the solvent to be used in the reaction with thiourea include alcohols such as methanol, ethanol and isopropyl alcohol, N,N-dimethylformamide, benzene, toluene, tetrahydrofuran and water. This reaction is carried out at a temperature of from 50° to 140° C. for 1 to 24 hours under stirring, preferably at a temperature of from 60° to 100° C. for 2 to 8 hours under stirring.

Industrial Applicability

The compound of the present invention shows a specific and high affinity for a sigma receptor. Accordingly it exhibits an antipsychotic action without causing any extrapyramidal disorders, which makes it useful as a remedy drug for, e.g., schizophrenia.

For this purpose, the compound of the present invention is mixed with a solid or liquid carrier and formulated into a pharmaceutical preparation suitable for oral or parenteral administration. Examples of the pharmaceutical preparation include solid preparations such as tablets, pills, capsules and granules, liquid ones such as injections, syrups and emulsions and preparations for external use such as ointments and suppositories, each of which can be prepared by the conventional formulation techniques.

The above-mentioned preparations may each contain additives conventionally employed in the art, for example, vehicles, binders, lubricants, stabilizers, wetting agents and emulsifiers. For example, an injection may contain a solubilizer such as distilled water for injection, physiological saline and Ringer solution and a preservative such as methyl paraoxybenzoate and propyl paraoxybenzoate. A syrup and an emulsion may contain sorbitol syrup, methyl-cellulose, glucose, sucrose syrup, hydroxyethylcellulose, edible oils, glycerol, ethanol and water as well as an emulsifier such as gum arabic and lecithin and a surfactant such as Tween and Span. A solid preparation may contain a vehicle such as crystalline cellulose, lactose, corn starch and mannitol, a lubricant such as magnesium stearate and talc, a binder such as hydroxypropylcellulose and polyvinylpyrrolidone, a disintegrating agent such as carboxymethylcellulose calcium and a flowability improver such as light silicic anhydride.

The dose of the compound of the present invention to a patient to be treated may vary depending on, for example, the age, disease and conditions of the patient. Usually, it may be administered to an adult in a dose of from 0.5 to 20 mg per day in one to several portions.

To illustrate the effects of the present invention in detail, the following Test Examples will be given.

TEST EXAMPLE 1 [Receptor Binding Test]

Male Wistar rats were employed as test animals.

Radiolabeled [$^3$H] (+)-3-PPP [3-(3-hydroxyphenyl)-N-n-propylpiperidine] was used as a compound specifically binding to a sigma receptor, while radiolabeled [$^3$H] (−)-sulpiride was used as a compound specifically binding to dopamine D2 receptor.

Reactions of these [$^3$H] compounds binding to the corresponding receptors were performed respectively in accordance with the following methods (1) and (2) described in Molecular Pharmacology, 32, 772 (1987), Journal of Pharmacy and Pharmacology, 32, 441 (1980) and Molecular Pharmacology, 32, 820 (1987).

(1) [$^3$H] (+)-3-PPP binding:

1 mg protein/ml of a membrane preparation obtained from the whole brain of rat (a membrane preparation containing sigma receptor), 2 nM of [$^3$H] (+)-3-PPP and a test drug were incubated in 1 ml of a 50 mM Tris-HCl buffer solution (pH 8.0) at 21° C. for 90 minutes.

(2) [$^3$H] (−)-sulpiride binding:

1 mg protein/ml of a membrane preparation obtained from rat striata (a membrane preparation containing dopamine D2 receptor), 2 nM of [$^3$H] (−)-sulpiride and a test drug were incubated in 1 ml of a 50 mM Tris-HCl buffer solution (pH 7.7) at 37° C. for 10 minutes.

After the completion of each reaction, the reaction mixture was filtered with suction into a glass filter (GF/B) and the radioactivity of the filter paper was measured with a liquid scintillation spectrometer.

The value obtained by using 10 μM of (+)-3-PPP or 10 μM of (−)-sulpiride with the [$^3$H] compound without any test drug in the above-mentioned method was referred to as the nonspecific binding of [$^3$H] (+)-3-PPP or [$^3$H] (−)-sulpiride, and the difference between the total binding (the value measured by adding no test drug) and the nonspecific binding was referred to as the specific binding.

By reacting the [$^3$H] compound at a definite concentration (2 nM) with the test drugs at various concentrations under the conditions as specified in the above (1) and (2), inhibition curves were obtained. On the basis of these inhibition curves, the concentration of each test drug causing 50% inhibition of the specific binding ($IC_{50}$) was determined. Table 1 shows the results.

TABLE 1

| Test Drug | Sigma receptor | | Dopamine D2 receptor | |
|---|---|---|---|---|
| | Inhibition % (1 μM) | $IC_{50}$ (nM) | Inhibition % (1 μM) | $IC_{50}$ (nM) |
| A | 93.1 | 8.7 | 57.0 | >1000 |
| B | 100.1 | 1.6 | −33.3 | >1000 |
| C | 99.7 | 3.2 | −31.0 | >1000 |
| 3-PPP | | 24.3 | | >1000 |
| Rimcazole | | 1460.0 | | 86000 |

(Note 1)
A: 2-Amino-4-(4-bromophenyl)-5-(2-di-n-pentylaminoethyl)-thiazole dihydrochloride.
B: 2-Amino-4-(4-bromophenyl)-5-(2-di-n-hexylaminoethyl)-thiazole dihydrochloride.
C: 2-Amino-4-(4-bromophenyl)-5-(2-di-n-octylaminoethyl)-thiazole dihydrochloride.
(Note 2)
As the data of rimcazole, those described in European Journal of Pharmacology, 155, 345 (1988) are cited.

The data of the D2 receptor are expressed in values for [$^3$H] spiperone binding.

TEST EXAMPLE 2 [Test on Action on (+)-SKF 100047-induced Abnormal Behaviors]

(Test animal)

Male ICR mice (Nippon Charles River) aged 4 to 5 weeks were divided into groups each having 10 animals and used.

(Test method)

Each animal was separately fed in a small transparent cage and fully familiarized with its environment. To the animals, test drugs A to C suspended in 5 % gum arabic at various concentrations were orally administered. After 30 minutes (after 35 minutes in the case of the test drug C), 30 mg/kg of (+) SKF 10047 (sigma receptor enhancer) was intraperitoneally administered to the animals. Since 10 minutes thereafter, stereotypical behavior scores were measured for 40 minutes at intervals of 5 minutes.

(Test drug)
 A: Rimcazole
 B: BMY 14802
 C: 2-amino-4-(4-bromophenyl)-5-(2-di-n-hexylamino-ethyl)thiazole dihydrochloride (Stereotypical behavior score)
 0: normal behaviors
 1: sniffing, standing up
 2: discontinuous movement, sniffing stronger than 1
 3: circling, moving backward
 4: continuous circling
 5: bending and stretching of limbs, head and neck (Calculation of $ED_{25}$)

The stereotypical behavior suppression ratio was determined on the basis of the sum of the scores of the test groups measured 8 times within 40 minutes by referring the sum of the score of a solvent (distilled water for injection) administered-group measured 8 times within 40 minutes as to 100%.

Each $ED_{25}$ value was calculated by determining the slope of a line of the suppression ratio formed by the method of least squares.

(Results)

Shown in Table 2.

TABLE 2

| Test Drug | $ED_{25}$ (mg/kg) |
|---|---|
| A | 37.9 |
| B | 7.6 |
| C | 0.019 |

Best Mode For Carrying Out The Invention

To illustrate the present invention more particularly, the following Example will be given.

Example

2-Amino-4-(4-bromophenyl)-5-(2-di-n-hexylaminoethyl)thiazole dihydrochloride

To a solution of 5.00 g of 4'-bromo-4-chlorobutyrophenone in 3 ml of toluene was added 11.1 ml of di-n-hexylamine and heated under reflux for 3 hours. After diluting with toluene, the reaction mixture was extracted with a 2N aqueous solution of hydrochloric acid. The extract was neutralized with a mass of sodium hydroxide and extracted with methylene chloride. Next, after drying over anhydrous magnesium sulfate, the solvent was distilled off under reduced pressure, thereby giving 4.88 g of crude 4'-bromo-di-n-hexylaminobutyrophenone.

This product was dissolved in 10 ml of methylene chloride and 7.4 ml of a 4N solution of hydrochloric acid in ethyl acetate was added thereto at room temperature. After distilling off the solvent under reduced pressure, 20 ml of acetic acid was added to the residue. Then 1.90 g of bromine was dropped thereto at room temperature and stirred at the same temperature for 1 hour. After distilling off the solvent under reduced pressure, 0.905 g of thiourea was added to a solution of the obtained residue in 20 ml of ethanol and then heated under reflux for 3 hours. 2N sodium hydroxide and methylene chloride were added to the reaction mixture. Then the organic layer was collected and dried over anhydrous magnesium sulfate and the solvent was distilled off under reduced pressure. To a solution of the obtained residue in 10 ml of methylene chloride was added 4.1 ml of a 4N solution of hydrochloric acid in ethyl acetate. After distilling off the solvent under reduced pressure, the residue was recrystallized from methylene chloride-isopropyl ether, thereby giving 3.51 g of the title compound.

m.p.: 149°–152° C.

The procedure of this example was substantially repeated except that the 4'-bromo-4-chlorobutyrophenone and di-n-hexylamine employed therein were substituted respectively by the corresponding materials. Thus the following compounds were obtained.

2-Amino-4-(4-bromophenyl)-5-(2-di-n-octylaminoethyl)thiazole dihydrochloride.

m.p.: 156°–158° C. (recrystallized from dichloromethane-isopropyl ether).

2-Amino-5-(2-di-n-hexylaminoethyl)-4-(4-fluorophenyl)thiazole dihydrochloride.

m.p.: 165°–168° C. (recrystallized from dichloromethane-isopropyl ether).

2-Amino-4-(4-bromophenyl)-5-(di-n-butylaminoethyl)thiazole dihydrochloride.

m.p.: 179.5°–182° C. (recrystallized from dichloromethane-isopropyl ether).

2-Amino-4-(4-bromophenyl)-5-(2-diisopentylamino-ethyl)thiazole.

m.p.: 117°–118.5° C. (recrystallized from dichloromethane-n-hexane).

2-Amino-4-(4-chlorophenyl)-5-(2-di-n-hexylamino-ethyl)thiazole (oily substance).

NMR (CDCl$_3$) δ (ppm); 7.58–7.29 (4H, m), 4.92 (1H, brs, exchangeable with D$_2$O), 3.00–2.80 (2H, m), 2.75–2.58 (2H, m), 2.56–2.30 (4H, m), 1.55–1.10 (16H, m), 0.88 (6H, t, J=6 Hz).

IR $v_{max}^{neat}$ cm$^{-1}$;

3284, 3118, 1627, 1532, 836, 724

MS m/e;

422 (M$^+$), 198 (100%)

Elemental analysis: as C$_{23}$H$_{36}$N$_3$SCl calculated (%): C, 65.45; H, 8.60; N, 9.96 found (%): C, 65.20; H, 8.72; N, 9.81

We claim:

1. An aminoalkylthiazole derivative represented by formula:

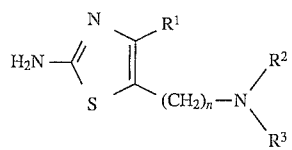
(wherein $R^1$ is 4-bromophenyl; $R^2$ and $R^3$ are either the same or different and each represents an alkyl group having 4 to 10 carbon atoms; and n is 2 or 3) and a salt thereof.
2. 2-amino-5-(2-di-n-butylaminoethyl)-4-(4-bromophenyl) thiazole dihydrochloride.
* * * * *